(12) United States Patent
O'Lenick

(10) Patent No.: US 8,613,912 B1
(45) Date of Patent: Dec. 24, 2013

(54) SILICONE ORGANO POLYESTERS

(71) Applicant: Thomas George O'Lenick, Dacula, GA (US)

(72) Inventor: Thomas George O'Lenick, Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 0 days.

(21) Appl. No.: 13/986,021

(22) Filed: Mar. 25, 2013

Related U.S. Application Data

(60) Provisional application No. 61/742,504, filed on Aug. 13, 2012.

(51) Int. Cl.
| | |
|---|---|
| *A61Q 5/12* | (2006.01) |
| *A61Q 7/00* | (2006.01) |
| *A61Q 5/00* | (2006.01) |
| *A61K 8/72* | (2006.01) |
| *A61K 8/18* | (2006.01) |
| *A01N 37/02* | (2006.01) |
| *A61K 31/225* | (2006.01) |

(52) U.S. Cl.
USPC ............... 424/70.12; 424/70.11; 510/119; 514/547

(58) Field of Classification Search
None
See application file for complete search history.

(56) References Cited

U.S. PATENT DOCUMENTS 7,344,708 B1    3/2008   LaVay
8,304,375 B1 *  11/2012  Wolff et al. ............ 510/138

* cited by examiner

*Primary Examiner* — Bethany Barham
*Assistant Examiner* — Danah Al-Awadi

(57) ABSTRACT

The present invention is directed toward a series of silicone/organic polymers with tunable ascetics, solubility, film formation and performance in cosmetic formulation. These novel polymers are designed with the three different hydroxyl containing monomers in the polyester. One is a siliphillic (silicone loving) and the other a oleophillic (oil loving) and the last hydrophilic (water loving). It is critical for there to be all three types of monomers linked together in a single polymer in order to make polymers in which solubility, spreadability, surface tension and film hardness can be altered for different cosmetic applications. When these groups are present a polymer there is a wide range of variation possible, making these polymers formulator friendly. The physical and chemical properties, including but not limited to: film formation of the current invention can be tuned rapidly by controlling the fatty group used, the degree of polymerization of the polymer, the molecular weight of the silicone polymer, the presence of ethylene oxide in the polymer backbone and the ratio of monomers to one another.

19 Claims, No Drawings

SILICONE ORGANO POLYESTERS

RELATED APPLICATION

This application claims priority to and benefit of U.S. Provisional Application No. 61/742,504 filed Aug. 13, 2013, the disclosure of which is incorporated herein for all purposes.

FIELD OF THE INVENTION

The present invention is directed toward a series of silicone/organic polymers with tunable ascetics, solubility, film formation and performance in cosmetic formulation. These novel polymers are designed with the three different hydroxyl containing monomers in the polyester. One is a siliphillic (silicone loving) and the other a oleophillic (oil loving) and the last hydrophilic (water loving). It is critical for there to be all three types of monomers linked together in a single polymer in order to make polymers in which solubility, spreadability, surface tension and film hardness can be altered for different cosmetic applications. When these groups are present a polymer there is a wide range of variation possible, making these polymers formulator friendly. The physical and chemical properties, including but not limited to: film formation of the current invention can be tuned rapidly by controlling the fatty group used, the degree of polymerization of the polymer, the molecular weight of the silicone polymer, the presence of ethylene oxide in the polymer backbone and the ratio of monomers to one another. Film formation, in this case is meant by the ability of this polymer to form a uniform "barrier" upon polymer dry down. This "barrier" or film can drastically improve the performance or cosmetic formulations. The film can be modified to tune the films performance. Tuned here is meant the ability to adjust the physical properties to a desired value. The resulting silicone copolymers have outstanding aesthetics and physical properties.

BACKGROUND OF THE INVENTION

Prior to the current invention, patents dealing with the use of dimethicone copolyol failed to recognize that there are significant structural differences between materials defined as dimethicone copolyols. Terminal dimethicone copolyols exist in two major forms.
Terminal Non-Alkoxylated

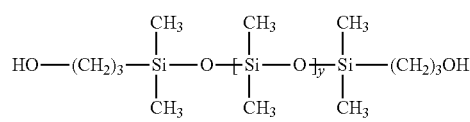

which are siliphillic
and
Terminal Alkoxylated

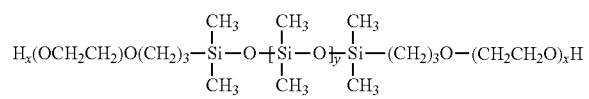

which have both siliphillic and hydrophilic portions.

None of the references above understood the desirability of incorporation of dimethicone copolyols into a polymer backbone will result in a random copolymer, together with diacids and organic crosslinkers, resulting in unique and heretofore unrecognized properties. The properties of these copolymers can be modified the physical properties in cosmetic formulation. Furthermore, the incorporation of a silicone polymer as a monomer, specifically a dimethicone copolyol, will provide superior surface activity when compared to an organic crosslinker; provide unparalleled aesthesis, and unique solubility. The flexibility that accompanies the dimethicone will allow for superior film flexibility and the lower surfaces tension allows for great spreadability and feel when compared to their organic homopolymer counterpart. The judicial control of the polymerization allows for the control of the solubility of these copolymers in alcohol, water, oil and silicone. Furthermore, the fatty groups allow for judicial control of physical, chemical and rheological properties of the polymer that will provide outstanding aesthesis when applied to hair, skin and fibers.

Along with the dimethicone and dimethicone copolyol, propane diol is used as a monomer in the polymerization. Propane diol is a common material of natural origin. The structure is:

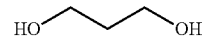

CAS Registry Number: 504-63-2 Index Name: Propane-1, 3-diol.

Propane diol is made from corn syrup effected by a genetically modified strain of *E. Coli* developed by DuPont Tate & Lyle Bioproducts. Propane diol is mainly used in the production of polymers such as polytrimethylene terephthalate, and formulated into a variety of industrial products including adhesives, laminates, coatings, aliphatic polyesters and moldings. Polymers synthesized with propane diol are made in a variety of ways.

THE INVENTION

Object of the Invention

The current invention is directed toward a series of silicone copolymers that are synthesized by the reaction of terminal dimethicone copolyol with a diacid, a mono-functional fatty alcohol and/or propane diol. This end capping allows for the product to have great aesthetics and solubility. The flexibility of the dimethicone also leads to a low glass transition temperature ($T_g$) and provides an extremely flexible polymer film. Furthermore, the presence of the dimethicone or dimethicone copolyol provide superior surface activity when in solution and water resistance when applied on the skin or hair. Propane diol can be used as a co-monomer in this reaction to modify the polymers performance. Regions of the random copolymer will contain propane diol, thus surprisingly and unexpectedly changes the flexibility of the polymer in that region. This drastically changes the film formation and film flexibility of the polymer film.

SUMMARY OF THE INVENTION

The present invention is related to a series of novel silicone copolymers that are prepared by the reaction of a terminal dimethicone copolyol, fatty alcohol, diacid and/or propane diol. The mono-functional fatty alcohol has a duel purpose in this polymerization: mono-functional monomers are commonly used to control the molecular weight of the polymer chain and are often referred to as a chain terminator. Once the chain terminator reacts onto the polymer backbone, the polymerization ceases. Chain terminators, being mono-functional, always end up on the end of the polymer chain. For this reason, the selection of the fatty groups and the diacid will drastically change the physical properties and cosmetic aesthetics of the resulting material.

The compounds of the present invention are made by the polymerization of a diacid, diacid, a fatty alcohol and/or propane diol. The resulting polymer has the film forming ability of the propane diol, and the surface activity or the dimethicone polymer but the end capping by the mono-functional fatty alcohol controls aesthetics and skin feel. This combination of groups results in a high efficient deposition of the skin, hair and fibers.

These polymers can be modified structurally to "tune" the overall aesthetics, solubility and film forming properties of a formulation based on the specific ratio of components reacted into a polyester. This ability to tune the aesthetics is easily demonstrated when considering the difference in the solubilities and flexibility of the monomers used. These polymers have very different solubilites depending upon the ratio of the groups reacted therein. This leads to superior surface activity in formulation and when applied on skin, fiber or hair.

DETAILED DESCRIPTION OF THE INVENTION

The present invention is aimed at a series of novel copolymers derived from dimethicone copolyol, diacid, and propane diol that provide desired esthetics and structure in cosmetic formulations.

Polyester

A polyester having the following structure:

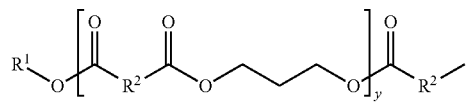

wherein,
$R^1$ is an alkyl containing 8 to 26 carbons, or mixtures thereof;
$R^2$ is independently selected from the group consisting of alkyl containing 2 to 12 carbons, alkyl having the following structures:

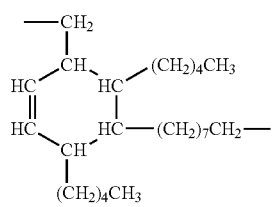

-continued and mixtures thereof;
x is an integer ranging from 3 to 10;
y is an integer ranging from 0 to 8;
b is an integer ranging from 10 to 30;
a is an integer ranging from 0 to 20.

Preferred Embodiment

In a preferred embodiment a is 0.
In a preferred embodiment a is an integer ranging form 1 to 20.
In a preferred embodiment a is an integer ranging form 5 to 20.
In a preferred embodiment a is an integer ranging form 5 to 10.
In a preferred embodiment a is an integer ranging form 10 to 15.
In a preferred embodiment $R^1$ is a guerbet alkyl containing 20 carbons.
In a more preferred embodiment $R^2$ is derived from dimer acid.

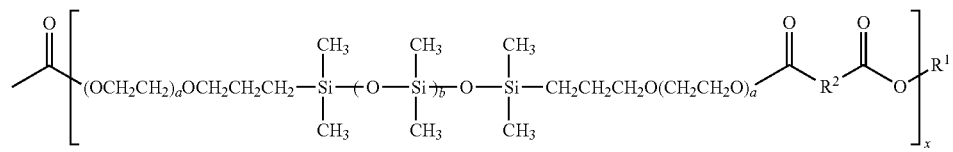

In a more preferred embodiment $R^1$ contains 32 carbon atoms.
In a more preferred embodiment $R^1$ contains 28 carbon atoms.
In a more preferred embodiment x is 8 and y is 2.
In a more preferred embodiment x is 2 and y is 8.
In a more preferred embodiment b is 10.
In a more preferred embodiment x is 5 and y is 5.
In a more preferred embodiment y is 0 and x is 10.

A process for conditioning skin, which comprises contacting the skin with an effective conditioning concentration of a polyester having the following structure:

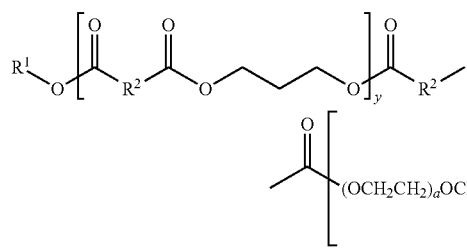
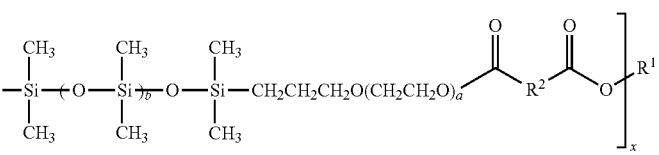

wherein,
$R^1$ is an alkyl containing 8 to 26 carbons, or mixtures thereof;
$R^2$ is independently selected from the group consisting of alkyl containing 2 to 12 carbons, alkyl having the following structures:

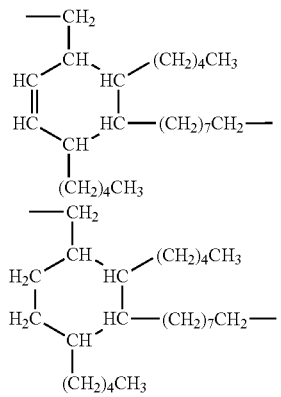

and mixtures thereof;
x is an integer ranging from 3 to 10;
y is an integer ranging from 0 to 8;
b is an integer ranging from 10 to 30;
a is an integer ranging from 0 to 20.

Preferred Embodiment

In a preferred embodiment the conditioning concentration ranges from 0.1 to 25% by weight.
In a preferred embodiment the conditioning concentration ranges from 1.0 to 25% by weight.
In a preferred embodiment the conditioning concentration ranges from 5 to 25% by weight.
In a preferred embodiment the conditioning concentration ranges from 5 to 15% by weight.
In a preferred embodiment the conditioning concentration ranges from 1 to 10% by weight.

Raw Materials
Fatty Alcohols

Fatty alcohols are useful in the practice of the present invention are items of commerce they are available as either single components or mixtures.

Fatty alcohols are useful as raw materials in the preparation of compounds of the present invention are commercially available from a variety of sources including Procter and Gamble of Cincinnati Ohio.

The structures are well known to those skilled in the art.

R—OH

| | Saturated | | |
|---|---|---|---|
| Example | R Formula | Common Name | Molecular Weight |
| 1 | $C_8H_{18}$ | Capryl | 130 |
| 2 | $C_{10}H_{22}$ | Capric | 158 |
| 3 | $C_{12}H_{25}$ | Lauryl | 186 |
| 4 | $C_{14}H_{30}$ | Myristyl | 214 |
| 5 | $C_{15}H_{32}$ | Pentadecyl | 229 |
| 6 | $C_{16}H_{34}$ | Cetyl | 243 |
| 7 | $C_{18}H_{36}$ | Stearyl | 269 |
| 8 | $C_{20}H_{40}$ | Arachidyl | 297 |
| 9 | $C_{22}H_{44}$ | Behenyl | 325 |
| 10 | $C_{26}H_{52}$ | Cetryl | 381 |
| 11 | $C_{34}H_{68}$ | Geddyl | 493 |

| | Unsaturated | | |
|---|---|---|---|
| Example | R Formula | Common Name | Molecular Weight |
| 12 | $C_{18}H_{36}$ | Oleyl | 268 |
| 13 | $C_{18}H_{34}$ | Linoleyl | 266 |

Example 14

Propane Diol

Propane diol is useful as raw materials in the preparation of compounds of the present invention. Propane diol is commercially available from DuPont Tate Lyle of Bloomington, Del.

The structures are well known to those skilled in the art.

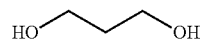

Example 15

Dimer Acid

Dimer acid is an item of commerce available commercially from Cognis Corporation. It conforms to the following structure:

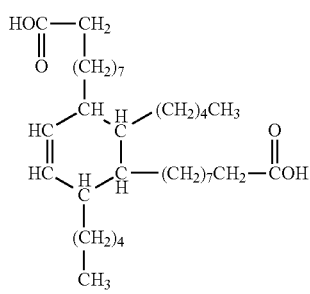

Example 16

Hydrogenated Dimer Acid

Hydrogenated dimer acid is an item of commerce available commercially from Henkel Corporation. It conforms to the following structure:

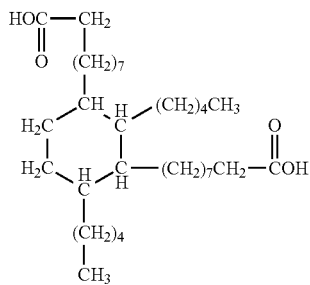

Dicarboxylic Acid

Dicarboxylic acid useful as raw materials in the synthesis of the compounds of the present invention are commercially available from a variety of sources including Cognis. They conform to the following structure;

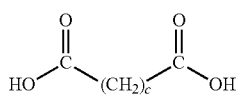

wherein;
c is an integer ranging from 1 to 10.

| Saturated Dicarboxylic acids | | | |
|---|---|---|---|
| Example | Common Name | C | Molecular Weight |
| 17 | Malonic | 1 | 104 |
| 18 | Succinic | 2 | 118 |
| 19 | Glutaric | 3 | 132 |
| 20 | Adipic | 4 | 146 |
| 21 | Pimelic | 5 | 160 |
| 22 | Subric | 6 | 174 |
| 23 | Azelaic | 7 | 188 |
| 24 | Sebacic | 8 | 202 |
| 25 | Undecanedioic | 9 | 216 |
| 26 | Dodecanedioic | 10 | 230 |

Guerbet Alcohols

Guerbet alcohols useful as raw materials in the preparation of compounds of the present invention are commercially available from a variety of sources including Sasol North America Incorporated of Houston Tex., and Jarchem located in Newark N.J.

The structures are well known to those skilled in the art.

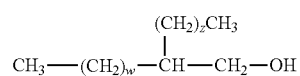

y is an integer ranging from 3-15 and x is an integer ranging from 5-17.

| Example | z | w |
|---|---|---|
| 27 | 9 | 7 |
| 28 | 11 | 13 |
| 29 | 13 | 15 |

Linear Dimethicone Copolyol) (a=0)

Linear Dimethicone copolyol are items of commerce available from SciTech LLC Lawrenceville, Ga. They conform to the following structure;

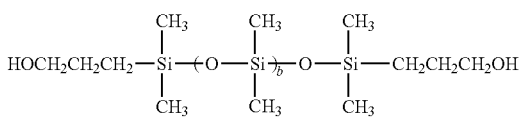

Wherein;
b is an integer ranging from 10 to 30.

| Example | B | Molecular Weight |
|---|---|---|
| 30 | 10 | 990 |
| 31 | 20 | 1,730 |
| 32 | 30 | 2,470 |

Linear Dimethicone Copolyol (LDMC) (a is greater than 0.)

LDMC are items of commerce available from SciTech LLC Lawrenceville, Ga. They conform to the following structure;

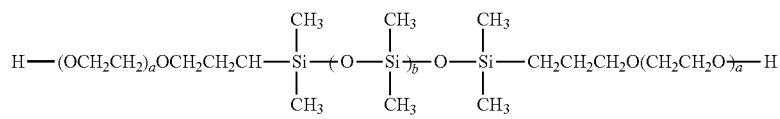

Wherein;
a is an integer ranging from 5 to 20;
b is an integer ranging from 10 to 30;

| Example | B | a | Molecular Weight |
|---|---|---|---|
| 33 | 10 | 5 | 1,025.0 |
| 34 | 10 | 10 | 1,245.0 |
| 35 | 10 | 20 | 1,685.0 |
| 36 | 20 | 5 | 1,764.0 |
| 37 | 20 | 10 | 1,984.0 |
| 38 | 20 | 20 | 2,424.0 |
| 39 | 30 | 5 | 2,504.0 |
| 40 | 30 | 10 | 2,724.0 |
| 41 | 30 | 20 | 3,164.0 |

The values above were determined by $^{13}$C NMR, $^{29}$Si NMR and Gel Permeation Chromatography and do not rely upon any trade names.

General Procedure

A specified number of grams propane diol (example 14) is added to a specified amount of Guerbet alcohol (examples 27-29), linear dimethicone copolyol (examples 30-32) and a diacid (examples 17-26). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | R$^1$ | | Propane Diol | R$^2$ | | Silicone | |
|---|---|---|---|---|---|---|---|
| Example | Example | Gram | Gram | Example | Gram | Example | Gram |
| 1 | 28 | 11.8 | 0.0 | 16 | 95.3 | 30 | 142.9 |
| 2 | 29 | 13.4 | 0.0 | 16 | 94.7 | 30 | 142.0 |
| 3 | 27 | 6.1 | 0.0 | 23 | 67.4 | 31 | 176.6 |
| 4 | 28 | 6.4 | 0.0 | 15 | 51.5 | 32 | 192.1 |
| 5 | 27 | 4.7 | 0.0 | 16 | 51.9 | 30 | 193.1 |
| 6 | 28 | 13.2 | 2.4 | 16 | 106.5 | 30 | 127.8 |
| 7 | 28 | 16.1 | 7.3 | 16 | 129.5 | 30 | 97.1 |
| 8 | 28 | 20.5 | 14.8 | 16 | 165.1 | 30 | 49.5 |
| 9 | 29 | 14.9 | 2.4 | 16 | 105.8 | 30 | 126.9 |
| 10 | 29 | 18.1 | 7.2 | 16 | 128.4 | 30 | 96.3 |
| 11 | 29 | 23.1 | 14.7 | 16 | 163.3 | 30 | 49.0 |
| 12 | 27 | 9.8 | 2.4 | 16 | 108.1 | 30 | 129.7 |
| 13 | 27 | 11.9 | 7.4 | 16 | 131.8 | 30 | 98.9 |
| 14 | 27 | 15.3 | 15.2 | 16 | 168.9 | 30 | 50.7 |
| 15 | 1 | 5.9 | 13.5 | 15 | 151.4 | 31 | 79.1 |
| 16 | 1 | 4.1 | 5.8 | 15 | 104.1 | 31 | 136.0 |
| 17 | 1 | 5.9 | 13.5 | 15 | 151.4 | 31 | 79.1 |
| 18 | 7 | 8.5 | 2.3 | 17 | 20.5 | 31 | 218.7 |
| 19 | 7 | 12.4 | 8.5 | 17 | 29.9 | 31 | 199.2 |
| 20 | 7 | 22.8 | 24.1 | 17 | 55.1 | 31 | 146.9 |
| 21 | 9 | 9.7 | 2.2 | 23 | 31.0 | 31 | 207.1 |
| 22 | 9 | 13.8 | 7.9 | 23 | 44.0 | 31 | 184.2 |
| 23 | 9 | 24.0 | 21.9 | 23 | 76.4 | 31 | 127.8 |
| 24 | 12 | 7.9 | 2.2 | 25 | 31.2 | 31 | 204.7 |
| 25 | 12 | 11.2 | 7.8 | 25 | 49.8 | 31 | 181.2 |
| 26 | 12 | 19.4 | 21.3 | 25 | 85.3 | 31 | 124.2 |
| 27 | 27 | 5.5 | 1.4 | 15 | 61.0 | 32 | 182.1 |
| 28 | 27 | 7.5 | 4.6 | 15 | 83.0 | 32 | 154.9 |
| 29 | 27 | 11.7 | 11.6 | 15 | 129.8 | 32 | 96.9 |
| 30 | 28 | 7.5 | 1.4 | 16 | 60.4 | 32 | 180.8 |
| 31 | 28 | 10.2 | 4.6 | 16 | 81.9 | 32 | 153.3 |
| 32 | 28 | 15.8 | 11.4 | 16 | 127.4 | 32 | 95.4 |
| 33 | 29 | 10.5 | 1.7 | 17 | 14.7 | 32 | 223.2 |
| 34 | 29 | 15.6 | 6.2 | 17 | 21.7 | 32 | 206.5 |
| 35 | 29 | 30.2 | 19.1 | 17 | 41.8 | 32 | 159.1 |
| 36 | 28 | 9.0 | 1.6 | 23 | 22.7 | 32 | 216.7 |
| 37 | 28 | 13.1 | 5.9 | 23 | 33.1 | 32 | 197.8 |
| 38 | 28 | 24.4 | 17.6 | 23 | 61.4 | 32 | 146.7 |

A specified number of grams propane diol (example 14) is added to a specified amount of Guerbet alcohol (examples 27-29), linear dimethicone copolyol copolyol (examples 30-32) and a diacid (examples 17-26). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | R$^1$ | | Propane Diol | R$^2$ | | Silicone Copolyol | |
|---|---|---|---|---|---|---|---|
| Example | Example | Grams | Grams | Example | Grams | Example | Grams |
| 39 | 28 | 10.3 | 0.0 | 16 | 83.0 | 34 | 156.6 |
| 40 | 29 | 11.7 | 0.0 | 16 | 82.6 | 34 | 155.8 |
| 41 | 27 | 4.7 | 0.0 | 23 | 52.5 | 38 | 192.8 |
| 42 | 28 | 5.9 | 0.0 | 15 | 47.7 | 40 | 196.4 |
| 43 | 27 | 4.3 | 0.0 | 16 | 48.0 | 34 | 197.6 |
| 44 | 28 | 11.7 | 2.1 | 16 | 94.1 | 34 | 142.1 |
| 45 | 28 | 14.6 | 6.6 | 16 | 117.7 | 34 | 111.0 |
| 46 | 28 | 19.5 | 14.1 | 16 | 157.1 | 34 | 59.3 |
| 47 | 29 | 13.2 | 2.1 | 16 | 93.5 | 34 | 141.2 |
| 48 | 29 | 16.5 | 6.6 | 16 | 116.8 | 34 | 110.2 |
| 49 | 29 | 22.0 | 13.9 | 16 | 155.5 | 34 | 58.7 |
| 50 | 27 | 8.6 | 2.1 | 16 | 95.4 | 34 | 143.9 |
| 51 | 27 | 10.8 | 6.7 | 16 | 119.6 | 34 | 112.9 |
| 52 | 27 | 14.5 | 14.4 | 16 | 160.5 | 34 | 60.6 |
| 53 | 1 | 5.3 | 12.0 | 15 | 134.4 | 38 | 98.4 |
| 54 | 1 | 3.4 | 4.8 | 15 | 85.5 | 38 | 156.4 |
| 55 | 1 | 5.3 | 12.0 | 15 | 134.4 | 38 | 98.4 |
| 56 | 7 | 6.3 | 1.7 | 17 | 15.2 | 38 | 226.8 |
| 57 | 7 | 9.4 | 6.5 | 17 | 22.7 | 38 | 211.5 |
| 58 | 7 | 18.5 | 20.3 | 17 | 44.6 | 38 | 166.6 |
| 59 | 9 | 7.3 | 1.7 | 23 | 23.2 | 38 | 217.8 |
| 60 | 9 | 10.7 | 6.1 | 23 | 34.0 | 38 | 199.2 |
| 61 | 9 | 199.9 | 18.1 | 23 | 63.4 | 38 | 148.6 |
| 62 | 12 | 6.0 | 1.7 | 25 | 26.5 | 38 | 215.9 |
| 63 | 12 | 8.7 | 6.0 | 25 | 38.6 | 38 | 196.7 |
| 64 | 12 | 16.0 | 17.7 | 25 | 71.1 | 38 | 145.1 |
| 65 | 27 | 5.1 | 1.3 | 15 | 56.8 | 40 | 186.8 |
| 66 | 27 | 7.0 | 4.4 | 15 | 78.1 | 40 | 160.6 |
| 67 | 27 | 11.2 | 11.2 | 15 | 124.9 | 40 | 102.7 |
| 68 | 28 | 7.0 | 1.3 | 16 | 56.2 | 40 | 185.6 |
| 69 | 28 | 9.6 | 4.3 | 16 | 77.1 | 40 | 159.0 |

-continued

|  | $R^1$ | | Propane Diol | $R^2$ | | Silicone Copolyol | |
|---|---|---|---|---|---|---|---|
| Example | Example | Grams | Grams | Example | Grams | Example | Grams |
| 70 | 28 | 14.2 | 11.0 | 16 | 122.6 | 40 | 101.2 |
| 71 | 29 | 9.6 | 1.5 | 17 | 13.4 | 40 | 225.4 |
| 72 | 29 | 14.4 | 5.7 | 17 | 20.0 | 40 | 209.9 |
| 73 | 29 | 28.2 | 17.9 | 17 | 39.2 | 40 | 164.7 |
| 74 | 28 | 8.3 | 1.5 | 23 | 20.8 | 40 | 219.4 |
| 75 | 28 | 12.2 | 5.5 | 23 | 30.6 | 40 | 201.7 |
| 76 | 28 | 23.0 | 16.6 | 23 | 57.9 | 40 | 152.6 |

The compounds of the present invention are oily materials that provide conditioning to skin. They retard transepidermal water loss, and provide a water resistant barrier on the skin. In emulsions, they provide a water resistance holding actives on the skin. The actives include sunscreen actives, antioxidants, peptides and vitamins.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A polyester having the following structure:

$$R^1-O-\left[\overset{O}{\underset{\|}{C}}-R^2-\overset{O}{\underset{\|}{C}}-O-CH_2CH_2CH_2-O\right]_y-\overset{O}{\underset{\|}{C}}-R^2-\overset{O}{\underset{\|}{C}}-$$

$$\left[-(OCH_2CH_2)_2OCH_2CH_2CH_2-\underset{CH_3}{\overset{CH_3}{\underset{|}{Si}}}-(O-\underset{CH_3}{\overset{CH_3}{\underset{|}{Si}}})_b-O-\underset{CH_3}{\overset{CH_3}{\underset{|}{Si}}}-\right.$$

$$\left.-CH_2CH_2CH_2O(CH_2CH_2O)_a-\overset{O}{\underset{\|}{C}}-R^2-\overset{O}{\underset{\|}{C}}-O-R^1\right]_x$$

wherein,

R$^1$ is an alkyl containing 8 to 26 carbons, or mixtures thereof;

R$^2$ is independently selected from the group consisting of alkyl containing 2 to 12 carbons, alkyl having the following structures:

$$-CH_2-CH-HC-(CH_2)_4CH_3$$
(with cyclohexene ring structure and $(CH_2)_7CH_2-$, $(CH_2)_4CH_3$ substituents)

$$-CH_2-CH-HC-(CH_2)_4CH_3$$
(with cyclohexane ring structure and $(CH_2)_7CH_2-$, $(CH_2)_4CH_3$ substituents)

and mixtures thereof;

x is an integer ranging from 3 to 10;
y is an integer ranging from 0 to 8;
b is an integer ranging from 10 to 30;
a is an integer ranging from 0 to 20.

2. A polyester of claim 1 wherein a is 0.

3. A polyester of claim 1 wherein a is an integer ranging from 1 to 20.

4. A polyester of claim 1 wherein a is an integer ranging from 5 to 20.

5. A polyester of claim 1 wherein a is an integer ranging from 5 to 10.

6. A polyester of claim 1 wherein a is an integer ranging form 10 to 15.

7. A polyester of claim 1 wherein R$^1$ contains 20 carbon atoms.

8. A polyester of claim 1 wherein R$^2$ is derived from dimer acid.

9. A polyester of claim 1 wherein R$^1$ contains 32 carbon atoms.

10. A polyester of claim 1 wherein R$^1$ contains 28 carbon atoms.

11. A polyester of claim 1 wherein x is 8 and y is 2.

12. A polyester of claim 1 wherein x is 2 and y is 8.

13. A polyester of claim 1 wherein b is 10.

14. A polyester of claim 1 wherein x is 5 and y is 5.

15. A polyester of claim 1 wherein y is 0 and x is 10.

16. A process for conditioning skin, which comprises contacting the skin with an effective conditioning concentration of a polyester having the following structure:

$$R^1-O-\left[\overset{O}{\underset{\|}{C}}-R^2-\overset{O}{\underset{\|}{C}}-O-CH_2CH_2CH_2-O\right]_y-\overset{O}{\underset{\|}{C}}-R^2-\overset{O}{\underset{\|}{C}}-$$

$$\left[-(OCH_2CH_2)_2OCH_2CH_2CH_2-\underset{CH_3}{\overset{CH_3}{\underset{|}{Si}}}-(O-\underset{CH_3}{\overset{CH_3}{\underset{|}{Si}}})_b-O-\underset{CH_3}{\overset{CH_3}{\underset{|}{Si}}}-\right.$$

-continued

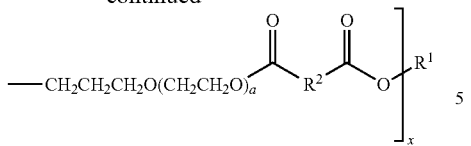

wherein,
R¹ is an alkyl containing 8 to 26 carbons, or mixtures thereof;
R² is independently selected from the group consisting of alkyl containing 2 to 12 carbons, alkyl having the following structure:

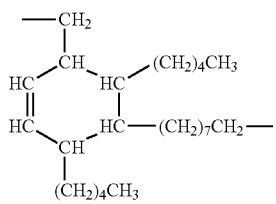

-continued

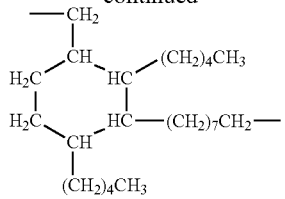

and mixtures thereof;
x is an integer ranging from 3 to 10;
y is an integer ranging from 0 to 8;
b is an integer ranging from 10 to 30;
a is an integer ranging from 0 to 20.

17. A process of claim 16 wherein the conditioning concentration ranges from 0.1 to 25% by weight.

18. A process of claim 16 wherein the conditioning concentration ranges from 1.0 to 25% by weight.

19. A process of claim 16 wherein the conditioning concentration ranges from 5 to 25% by weight.

* * * * *